United States Patent [19]
Alexandre

[11] Patent Number: 4,944,677
[45] Date of Patent: Jul. 31, 1990

[54] INTRAOSSEUS DENTAL ANESTHESIA APPARATUS AND METHOD

[75] Inventor: Raymond J. Alexandre, 18, Rue Lamartine, Fort de France 97200 Martinique, France

[73] Assignees: Raymond Joseph Alexandre, Martinique, France; Richard P. Masel, Newton, N.J.

[21] Appl. No.: 67,153

[22] Filed: Jun. 29, 1987

[51] Int. Cl.$^5$ ............................................. A61C 3/02
[52] U.S. Cl. .................................. 433/165; 433/134; 606/80
[58] Field of Search .............. 128/92 VD, 305.1, 310, 128/311; 433/134, 165, 173; 604/188

[56] References Cited
U.S. PATENT DOCUMENTS 2,317,648  4/1943  Sigveland ............................. 433/80
3,893,445  7/1975  Hofsess ............................. 128/754

OTHER PUBLICATIONS

"New Inventions: A Needle Trephine", by Dr. George W. Smith, from the Sep. 6, 1958 issue of The Lancet, p. 509.

Primary Examiner—Martin P. Schwadron
Assistant Examiner—Allen J. Flanigan
Attorney, Agent, or Firm—Buttmi and Greenfield

[57] ABSTRACT

An apparatus for the intraosseous administration of a dental anesthesia comprising, in a single unit, drilling means, a connecting flange, and a mandrel for removable engagement with a notable power source, all lying on the same central axis; a mandrel for fabrication of such apparatus from a conventional disposable dental needle; a kit including such apparatus in combination with a disposable dental needle and a hypodermic syringe; and a method for using such apparatus.

12 Claims, 1 Drawing Sheet

INTRAOSSEUS DENTAL ANESTHESIA APPARATUS AND METHOD

BACKGROUND OF THE INVENTION

1. Field of the Invention

This invention relates to intraosseous dental anesthesia, an apparatus for effecting such anesthesia, and a method for using such apparatus.

2. Statement of Related Art

Dental anesthesia is generally by a topical anesthesia injection followed by a deeper injection which blocks off the nerve endings within the region (infiltration) or blocks off the sensory nerves at some distance from the region (nerve blocking). It is extremely desirable to minimize the amount of anesthesia injected, since toxic reactions may result from drug sensitivity or misdirection of the injection needle into the bloodstream, which reactions may be so severe as to cause convulsions or cardiac or respiratory failure (see The Merck Manual, 13th ed., (1977) Merck & Co., Rahway, N.J. U.S.A. at 226). Moreover, misplacement of the hypodermic needle or even a slight error in placement may necessitate further injections, raising the risk of such toxic reactions. Furthermore, conventional anesthesia results in numbness of the tongue, cheek, and/or lips or even part of the face during the dental procedure and for some time afterward. This is very discomforting for the patient.

Ideally, an apparatus and/or method for dental anesthesia injection should have various positive attributes, including:

1. Almost immediate effectiveness (within one minute or less);
2. Effectiveness for both maxillary (upper jaw) and mandibular (lower jaw) applications;
3. Simplicity of application;
4. Minimal special apparatus;
5. Capability of utilizing various points of penetration;
6. Capability of administration with minimal pressure, so as to avoid causing pain;
7. Capability of administration outside of septic area;
8. Minimal chance of injection into blood vessels; and
9. Minimal post-operative effects.

Conventional methods of dental anesthesia, include the following.

I. Injection into mucous tissue
  A. Advantages:
    1. Ease of application;
    2. Injection possible with minimal pressure;
    3. Efficient for both maxillary and mandibular application;
  B. Disadvantages:
    1. Too long before anesthesia takes effect (about 5 minutes);
    2. The amount of anesthesia is high (about 4 cc);
    3. Requires adrenalin or another vaso conductor, with cardiac patients;
II. Injection into a ligament
  A. Advantages:
    1. May be injected near the apex of the tooth;
    2. Is effective in about 1 minute;
    3. Efficient for both maxillary and mandibular application;
  B. Disadvantages:
    1. Requires high pressure for injection, causing pain;
    2. Injection is into a septic area;
    3. Risk of infection of the ligament is increased;
    4. May increase post-operative problems, including inflammation and necrosia;
III. Injection into the septum
  A. Advantages:
    1. Requires small amount of anesthesia (about 1 cc);
    2. Anesthetic effect is immediate (1 minute or less);
    3. Efficient for both maxillary and mandibular application;
    4. Minimal after effects (numbness);
  B. Disadvantages:
    1. Injection requires strong pressure, making it very painful;
    2. Exact positioning of needle is required;
    3. Injection is into a septic area;
IV. Injection near the nerve-trunk (nerve blocking)
  A. Advantages:
    1. Very effective;
    2. Avoids post-operative inflammation or infection;
  B. Disadvantages:
    1. Long delay in effecting anesthesia (10 minutes or more);
    2. High risk of injection into a blood vessel, potentially dangerous to some patients;
    3. Post-operative numbness is very long lasting.

As can be seen from the above, none of the conventional methods for dental anesthesia is without serious disadvantages. The only remaining anesthetic method involving the local administration of an anesthesia for dental work, is intraosseous anesthesia (i.e. injection into the jawbone itself, as contrasted into soft tissue or into the ligament/septum).

Intraosseous dental anesthesia, when properly used, affords a profound numbness limited only to the tooth to be treated.

U.S. Pat. No. 2,317,648 — Siqveland, discloses a particular apparatus for intraosseous dental anesthesia, and a method for its use. However, the disclosed apparatus is not in use today, although this patent was granted in 1943. In the Siqveland patent, a threaded sleeve is concentrically and removably positioned around a drill bit, shown as element 15 in FIG. 5. The drill bit 15 as illustrated is of conventional, solid, mechanical drill bit configuration. The drill bit 15 at its non-boring end is connected to a flange 17 which is itself connected to a shank 16 adapted to be connected to a contra-angle. The patent teaches away from the use of the drill bit 15 without the threaded sleeve 20 surrounding it. The combination drill bit/threaded sleeve penetrates the bone, and the drill bit is then detached and withdrawn, leaving the threaded sleeve embedded in the bone as a guide for a hypodermic needle. After injection of the anesthesia, the threaded sleeve is withdrawn from the bone by reverse rotation. A spring and gasket means is used to operate the parts simultaneously. Thus, the patented device comprises at least 3 separate elements, all of very small size, which must be connected and disconnected during its utilization. U.S. Pat. No. 2,317,648 also discloses as background information (page 1, lines 27–39) an "old" method which is called "intraosseous". However, the old method involves drilling a hole into the side of the tooth. This method is not intraosseous, since a tooth is not bone. The subject invention does not contemplate drilling into a tooth to effect anesthesia.

SUMMARY OF THE INVENTION

This invention affords a device for effecting intraosseous dental anesthesia. The device comprises a mandrel adapted to be connected to a power source at one end and to a bone penetrating means at the other end. The bone penetrating means is a smooth needle with a beveled point, but without a helical cutting edge, which must be hollow. The mandrel may be directly connected to the penetrating means or connected through a flange. The device may be of unitary construction, or the needle, flange, and mandrel may comprise different materials which are removably or permanently joined to each other.

This invention also affords a method of effecting intraosseous dental anesthesia using the above described device comprising: (1) using the device to drill a hole into the jawbone near the apex of the tooth to be anesthetized (with optional prior topical anesthesia); (2) removing the device from the jaw; (3) inserting a hYpodermic needle of substantially the same gauge as the bone penetrating means into the hole thus formed, and (4) injecting an anesthesia-effective amount of anesthetic.

DETAILED DESCRIPTION OF THE INVENTION

Apparatus

The apparatus according to this invention comprises a drilling means linearly attached along a common axis to a mandrel by means of a hub or flange. The drilling means and flange are permanently attached to one another. The mandrel is permanently attached to the flange in a preferred embodiment, but may also be removably attached.

Figure 1:
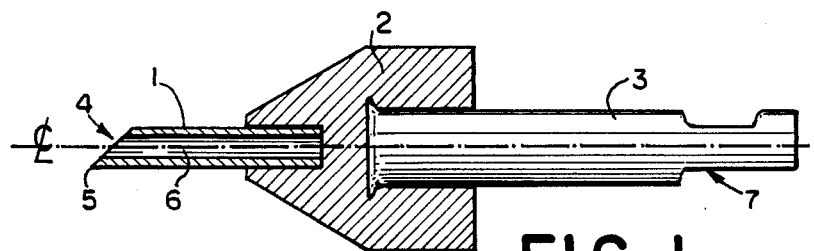
FIG. 1 is a cross-sectional view of an embodiment according to this invention.
Figure 2:
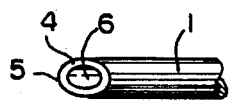
FIG. 2 is an enlarged top plan view of a portion of FIG. 1.

In FIGS. 1 and 2, drilling means 1 comprises a surgical needle with a hollow center 6 and a beveled edge 4. The beveled edge 4 has a cutting point 5 which effects almost all of the drilling. The non-cutting end of the needle 1 is permanently positioned within one end of a connecting flange 2, and a mandrel 3 is permanently positioned within the other end, the central axes of the drilling means 1 and mandrel 3 being on the same line. The free end of the mandrel 3 is adapted for insertion into a conventional dental power means, such as a contra-angle, and for this purpose optionally may have an annular, or semi-annular, or other locking means 7.

The drilling means must comprise a needle of surgical steel, or the like, of which at least the cutting point 5 must be of sufficient hardness to drill through the alveolar plate surrounding a bone, for a distance of about 2 mm. The outer surface of the drilling means should be substantially cylindrical and free of burrs or other surface imperfections, so that a clean hole can be drilled, penetrating first through the tissue surrounding the bone and then into the bone itself. Although an expandingly tapered drilling means may be used, it is not required. The drilling means should not have a helical cutting edge in the manner of mechanical drill bits, since this is impractical to achieve with the preferred small gauge of the drilling means, and also since this may permit potentially irritating bits of removed bone to remain in the bone. The beveled edge of the drilling means thus acts as the only cutting edge. The angle of the bevel may be within the range of 15 to 75° to the central axis, and is preferably that found in standard beveled edge disposable injection needles. It is preferred that the drilling means has a hollow center 6, which acts to collect bits of bone which are removed. Thus, the drilling means may comprise a disposable dental needle of the type used for anesthetic injection, although that end of the needle fastened to the hub or connecting flange 2 is necessarily permanently sealed. Since it is important that the drilling means is only minimally flexible (as contrasted with most dental needle), it should project about 4 to 12 mm preferably about 5 to 7 mm beyond the connecting flange 2. The diameter of the drilling means 1 may be 25 to 35 gauge, although a gauge as small as 35 may be too flexible and a gauge as large as 25 may create an unnecessarily large bore. A 30 gauge drilling means is therefore preferred.

Figure 3:
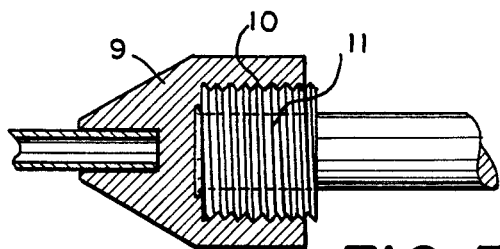
FIG. 3 is a cross-sectional view of part of another embodiment according to this invention.
Figure 4:
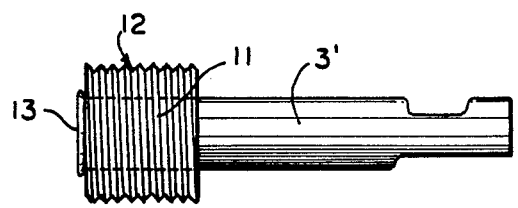
FIG. 4 is a side plan view of the mandrel and mandrel collar of FIG. 3.

The connecting flange or hub 2, as shown in FIG. 1, may comprise a metal (preferably surgical steel) or a tough, substantially rigid, plastic such as a polyamide, polytetrafluorethylene, or the like. Rigidity of the hub 2 is desirable to prevent wobble in the drilling means while the apparatus is in use. As shown in FIG. 2, the connecting flange or hub 2 is solid and comprises one piece. However, it may comprise more than one piece (as shown in FIGS. 3, 4), and may be at least partially hollow, provided that the drilling means and mandrel are held in rigid alignment with each other along a common axis, (shown as a center line in FIG. 1). The configuration of the connecting flange 2 is not critical, although functional and material considerations dictate that it is preferably a 5 to 10 mm diameter cylinder with a frustoconical end from which the drilling means projects. The frustoconical configuration permits greater visibility of the point of entry, by the dental practitioner.

The drilling means 1 and hub 2 are obtainable commercially as a single unit, known as a "disposable dental needle", and sold under various trademarks as well as generically. Disposable dental needles are designed to fit on the end of a dental syringe, and are available with either a substantially rigid plastic hub or a metal hub. Either of such could be utilized in this invention. Although disposable dental needles are commercially available with either metal or plastic needles, only those with good quality metal needles should be used in this invention, since the "cutting" edge of a available beveled plastic needles would be too soft. However, if fashioned of a suitably tough plastic, even a plastic needle (i.e. drilling means 1) could be used in this invention. Disposable dental needles are available in sizes "extra-long, long, short and extra-short", of which short or extra-short are useful in this invention. These commercial needles also are available in gauges 23, 25, 27, and 30, among others, of which 30 gauge is preferred for this invention. The commercially available dental needles all comprise a hollow connecting flange, an embodiment of which may be seen in FIG. 3. Since the disposable dental needles are all designed to receive a cartridge ampule (carpule) of anesthetic opposite the end penetrating the gum, the needle projects inwardly of the cuplike connecting flange 2 and generally beyond it, so that it can engage the carpule. When fabricating the inventive device from such a commercially available disposable dental needle, this inwardly projecting end can be shortened, or the mandrel can have a hollow receiving bore that will fit over it.

The mandrel 3 comprises a generally rod-like configuration, which may end in a butt-plate 13, an example of which is shown in FIGS. 3, 4. The butt-plate 13 may be in the form of an annular lip, and acts to anchor the mandrel 3 into the one-piece connecting flange 2 of FIG. 1, or to a mandrel collar 11 as shown in FIGS. 3, 4. The mandrel may comprise a bore (not shown) adapted to receive an inwardly projecting drilling means 1 or may be solid as shown in FIG. 1 when the drilling means does not project inwardly enough to meet it. The free end of the mandrel 3 is adapted to be received by a rotating power means (not shown). Depending upon the nature of the power means, the free end of the mandrel 3 may be a simple cylindrical solid, preferably with a chamfered edge, or may be in any configuration suitable to the power means. The configuration of the free end of the mandrel (3) is not critical to this invention, although a locking means 7 such as illustrated in FIG. 1 is preferred, such means comprising an annular groove and a notched tip. The length of the mandrel 3 projecting beyond the plane of the end of the connecting flange 2, 9 is equivalent to the length of the shank of a standard dental bur or cutter, a length of about 10 to 16 mm being conventional. The diameter of the free end of the mandrel 3 should also be equivalent to that of a standard bur or cutter for example, about 1.5 to 2.5 mm, approximately 2 mm being conventional. The material of the mandrel may be a metal alloy such as steel, or a plastic tough enough to withstand torsional stress, such as a nylon or other polyamide. The material of the mandrel 3 is not considered to be critical to this invention, provided that it can withstand the indicated torsional stress originating from the power means, and is sufficiently rigid to control the drilling means while it is boring into the bone.

In an alternate embodiment of this invention, shown in FIGS. 3, 4 a hollow connecting flange 9 is utilized, as discussed above, in which instance the mandrel 3 is best fitted with a mandrel collar 11, one embodiment of which is illustrated in FIG. 4. The mandrel collar 11 should be of a complementary shape and configuration to the hollow inner portion of the connecting flange 9, so that it can be inserted therein with a close friction fit. Since it is critical that the entire apparatus be rotated by the power means to effect drilling into the bone, it is also critical that none of the component parts (i.e. drilling means 1, flange 2 or 9, and mandrel 3, or mandrel 3 and mandrel collar 11) rotate with respect to each other. This may be effected by gluing the mandrel 3 into the hollow connecting flange or hub 9, using any thermoplastic or thermosetting glue that can withstand the stresses put upon the apparatus. Alternatively, the mandrel 3 and hollow connecting flange 9 may have one or more complementary planar surfaces, and other (structural) means may be incorporated for locking these elements non-rotationally together. The mandrel collar 11 may be secured to the mandrel 3 by means of a butt plate 13, or simply by using a mandrel end with other than a cylindrical configuration.

In a particularly preferred variant of the alternate embodiment, specifically shown in FIGS. 3, 4, the inner cylindrical surface of the hollow connecting flange 9 may comprise a female thread 10. A disposable dental needle with such a configuration is commercially available from the Septodent Company, under the trademark "Rotaject". If the apparatus of this invention is fabricated using the "Rotaject" disposable dental needle, then the mandrel collar 11 should have a complementary male thread 12. Despite a tight threaded fit, it is advisable that the hollow connecting flange 9 and mandrel 3/mandrel collar 11 be glued together or otherwise bonded, to prevent rotational slippage. This invention also contemplates affording this mandrel 3/mandrel collar 11 alone, for use with a "Rotaject"-type disposable dental needle.

The power means useful in connection with this invention include any conventional dental handpiece adapted to receive the free end of the mandrel 3. The power means does not constitute a part of this invention. Such power means generally comprise a motor (power unit) which may be an electric motor or pneumatic motor; a front end with or without a torque multiplier; and an angle which may be a contra-angle with a latch or friction grip, a gear reduction latch-type contra-angle, or a prophy-angle. The drilling into the bone is best accomplished at a relatively low speed (about 8,000–12,000 rpm) and may require relatively high torque, so any handpiece affording these characteristics may be employed. From experience, a latch-type contra-angle designed for low speed, has proven to be very efficacious. The handpiece most frequently used for restoring a tooth is usually operated at 100,000 to 300,000 rpm. Therefore, it may be useful to employ a slow speed handpiece of the type used in implants.

In addition to affording the above-described intraosseous drilling apparatus, the present invention contemplates a kit comprised of: at least one, preferably 10 to 30, disposable intraosseous drilling apparati as described herein; an equal number of disposable dental needles of conventional configuration whose gauge must be the same as the gauge of the drilling means (preferably 30 gauge-short), and a conventional syringe adapted to receive the disposable dental needles.

Method

The method of this invention may employ the intraosseous drilling apparatus and kit above described. Generally, the method comprises: drilling into the maxillary superior or mandible in the vicinity of the apex of the one or more teeth to be anesthetized utilizing intraosseous drilling means such as described herein, until the cortical plate is penetrated; removing the drilling means from the bore so formed; and injecting and effective amount of anesthesia through the bore into the spongy mass of the bone which lies beyond the cortical plate.

More specifically, this invention affords a method for dental anesthesia comprising the following sequential steps.

Figure 5:
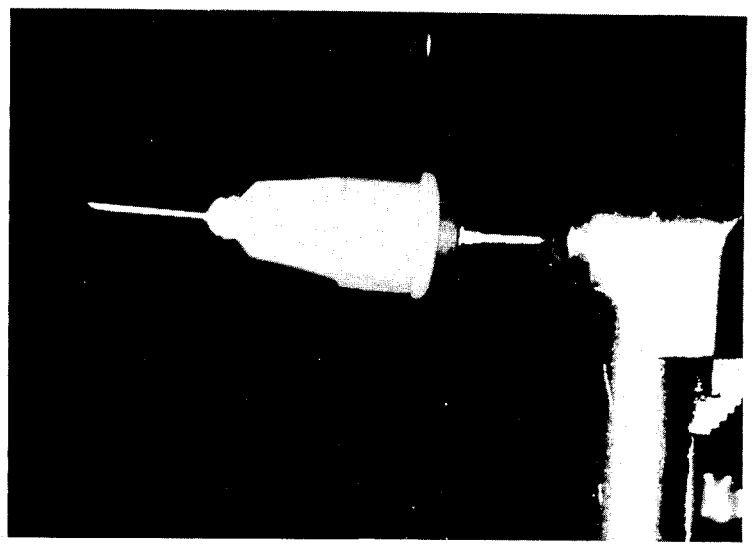
FIG. 5 is a photograph of an embodiment according to this invention attached to a latch-tYpe contra-angle power means.
Figure 6:
FIG. 6 is a photograph illustrating a method for using the embodiment of FIG. 5 to drill into the mandible of a patient.
Figure 7:
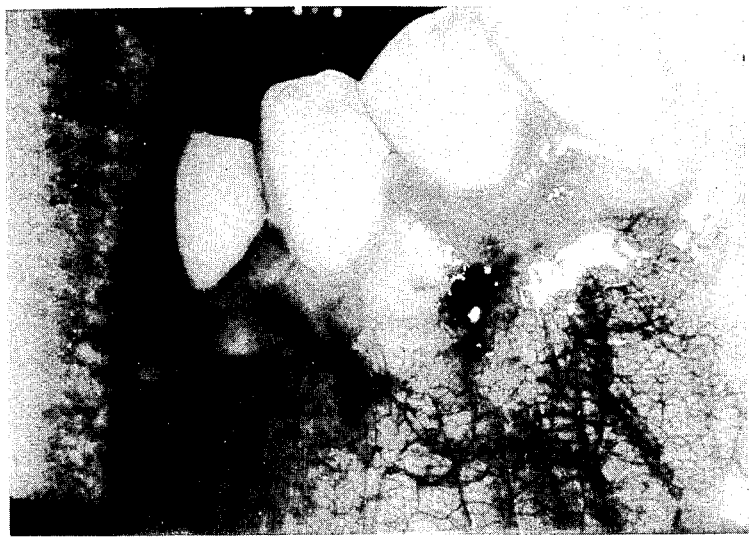
FIG. 7 is a photograph of the patient in FIG. 6 after the drilling means has been withdrawn, showing the characteristic spot of blood that is formed.
Figure 8:
FIG. 8 is a photograph showing insertion of an anesthetic syringe into the hole drilled into the mandible, as marked by the blood spot of FIG. 7.

1. Anesthetizing the surface of the gum in the area in which anesthesia is to be administered, typically by injecting one drop of anesthetic into the gum in that area.
2. Inserting an intraosseous drilling assembly of the type described herein into a contra-angle (preferably latch-type) as shown in FIG. 5, and positioning the point of the drilling means 1 at the spot where it is intended to drill. The spot chosen should be directly above (maxillary) or below (mandible) the apex of the tooth to be anesthetized, or a central tooth if more than one is to be anesthetized. Drilling should never be into the tooth itself, but rather into that portion of the maxillary superior or mandible closest to it, typically 2–10 mm from the apex. The position of the contra-angle should be chosen carefully, so that the drilling means 1 will penetrate into the desired spot.
3. With the handpiece rotating at 8,000 to 12,000, (preferably 9,000 to 11,000, most preferably about 10,000 rpm), penetrating through the gum and, slowly and with minimal pressure, continuing until the cortical plate is penetrated and the spongy mass of the bone has been reached (about 1 to 4 mm). This can be detected by feel, since the spongy mass offers less resistance to the drilling means. This step is illustrated in FIG. 6.
4. Removing the intraosseous drilling apparatus and contra-angle from the patient. It should be noted that a single drop of blood will form which marks the entrance to the drill bone. This step is illustrated in FIG. 7. The initial anesthesia is particularly useful in that it hardens the gum and thus contributes to formation of only a single drop of blood.
5. Noting the location of the above single drop of blood, inserting the needle of a hypodermic syringe (previously loaded with anesthetic), into the drilled bone, keeping the needle of the syringe at the same angle as that of the drilling means (1), and slowly injecting anesthesia directly into the spongy mass of bone closest to the apex of the tooth to be anesthetized. This step is illustrated in FIG. 8. The injection of anesthesia will be virtually painless, provided that it is done slowly, and thus under low pressure, preferably at a constant rate.

In using the method of this invention, it is critical that the hypodermic dental needle be of the same or even 1 or 2 gauges smaller than the gauge of the drilling means, the identical gauge being very much preferred. This gauge is, as indicated, most preferably no. 30. It is generally advantageous to employ the syringe and needle for both the optional surface anesthesia of step 1, and the deep anesthesia of step 5.

The nature of the anesthesia used in this method is not critical, and any anesthesia such as lidocaine, mepivicaine, prilocaine, bupivicaine, or novocaine, may be employed. A very important benefit of the inventive method, is that regardless of type, the amount of anesthesia necessary is greatly reduced. Typically, a half carpule (about 1 cc) of anesthesia is adequate to achieve profound anesthesia for one, two, or even three teeth. As discussed above, this is remarkably less anesthesia than is normally required to achieve the same numbing effect, and because of this and the situs of application, it is possible to anesthetize cardiac patients without the need for adrenaline.

Further advantages of the method of this invention are: that the anesthesia is almost immediate (taking place in 1 minute or less); there is minimal pain in the anesthesia administration; virtually any location in the maxillary superior or mandible may be anesthetized; and the administration is outside of the septic zone, thus reducing the risk of inflammation, infection, necrosis, or the like.

The theory behind intraosseous anesthesia, although not limiting of this invention, is quite simple. The nerves going to each tooth enter at its apex (or apexes) and pass through that part of the jaw to which the tooth is attached (either the maxillary superior or the mandible). In injecting anesthesia into the spongy mass of the jaw, it diffuses only slightly before it reaches the nerve entering the tooth apex. Thus, the major portion of the anesthesia is used solely to anesthetize the desired tooth. This method does not totally eliminate the possibility of some anesthesia entering the bloodstream, since blood capillaries are present in the spongy mass of the bone. However, it virtually eliminates the possibility of injection directly into an artery or vein, and minimizes the amount of anesthesia required, thus substantially reducing the risk of shock to the heart.

Conventionally, because the mandible is very thick, anesthesia is usually administered as a nerve block at the back of the jaw, which may numb as much as a quadrant, and which uses a large amount of anesthesia. Furthermore, nerve blocks of this type frequently require repeated anesthesia administration. The most commonly used alternative of intraligament injection (discussed above) in addition to the stated disadvantages is difficult for many practitioners because of its use of a long, fine, needle. For these reasons, the intraosseous anesthesia method of this invention is particularly useful for anesthetizing a tooth in the mandible, particularly where it is "hot" (painful) and does not respond well to a nerve block.

I claim:
1. An apparatus for enabling the intraosseous injection of dental anesthesia comprising:
   means for drilling a hole in a jawbone comprising a hollow needle of from about 25 to 35 gauge having a drilling end with a substantially smooth and uniform cylindrical surface and a beveled tip and attached end, said bevelled tip being formed by a single planar cut through said hollow needle at an angle of 15 to 75 degrees to the longitudinal axis of said hollow needle;
   a connecting flange to which the fastened end of said drilling means is permanently fastened; and
   a mandrel lying on a common axis with said drilling means, having a free end adapted for engagement with a dental handpiece and a fastened end which is permanently or removably fastened to said connecting flange, projecting in a direction opposite to said drilling means.
2. The apparatus of claim 1 wherein said mandrel is a rod projecting about 10 to 20 mm having a diameter of about 1.5 to 2.5 mm.
3. The apparatus of claim 1 wherein said mandrel further comprises locking means at its free end, for removable locking engagement with a power means for rotating said apparatus.

4. The apparatus of claim 1 wherein said needle is about 30 gauge and projects about 4 to 12 mm from said connecting flange.

5. The apparatus of claim 1 wherein said needle is about 30 gauge and projects about 5 to 7 mm from said connecting flange.

6. The apparatus of claim 1 wherein said connecting flange is a cylinder tapering to a frustocone at the end to which said drilling means is attached, lying on a common axis with said drilling means and said mandrel.

7. The apparatus of claim 1 wherein:
said drilling means comprises a hollow needle with a substantially smooth and uniform cylindrical surface and a beveled tip, is about 25 to 35 gauge, and projects about 4 to 12 mm from said connecting flange;
said connecting flange is a cylinder tapering to a frustocone at the end to which said drilling means is attached, lying on a common axis with said drilling means and said mandrel; and
said mandrel is a rod projecting about 10 to 16 mm, having a diameter of about 1.5 to 2.5 mm, and further comprising locking means at its free end, for removable locking engagement with a power means for rotating said apparatus.

8. The apparatus of claim 1 wherein said drilling means, connecting flange, and mandrel, are each independently comprised of metal or a rigid plastic.

9. The apparatus of claim 7 wherein said drilling means, connecting flange, and mandrel are each independently comprised of metal or a rigid plastic.

10. A kit for effecting intraosseous dental anesthesia comprising, in combination, at least one apparatus according to claim 1, an equal number of disposable dental needles of the same gauge and length, and a hypodermic syringe adapted to receive said disposable dental needles.

11. A mandrel comprising a rod of 10 to 25 mm length with a diameter of about 1.5 to 2.5 mm having at one end thereof an annular mandrel collar threadably engaged with a cuplike hub having affixed thereto a disposable 25 to 35 gauge dental needle about 4 to 12 mm in length, said needle being hollow and having a bevelled tip formed by a single planar cut through said needle at an angle of 15 to 75 degrees to the longitudinal axis of the needle.

12. The mandrel of claim 11, wherein the free end of the rod includes locking means for removable engagement with power means for rotating the mandrel.

* * * * *